US008790913B2

(12) United States Patent
Zeikus

(10) Patent No.: US 8,790,913 B2
(45) Date of Patent: Jul. 29, 2014

(54) METHODS OF USING PNEUMATIC BIOREACTORS

(75) Inventor: J. Gregory Zeikus, Okemos, MI (US)

(73) Assignee: PBS Biotech, Inc., Camarillo, CA (US)

( * ) Notice: Subject to any disclaimer, the term of this patent is extended or adjusted under 35 U.S.C. 154(b) by 985 days.

(21) Appl. No.: 12/884,431

(22) Filed: Sep. 17, 2010

(65) Prior Publication Data

US 2011/0003366 A1  Jan. 6, 2011

Related U.S. Application Data

(63) Continuation-in-part of application No. 11/739,089, filed on Apr. 23, 2007, now abandoned, and a continuation-in-part of application No. 12/606,519, filed on Oct. 27, 2009, now Pat. No. 7,819,576, which is a continuation of application No. 11/258,742, filed on Oct. 26, 2005, now Pat. No. 7,628,528.

(51) Int. Cl.
| | |
|---|---|
| *C12N 1/12* | (2006.01) |
| *A01G 7/00* | (2006.01) |
| *C12M 1/02* | (2006.01) |
| *B01F 7/04* | (2006.01) |
| *C12M 1/00* | (2006.01) |
| *B01F 7/22* | (2006.01) |
| *C12M 1/12* | (2006.01) |
| *B01F 7/00* | (2006.01) |
| *C12M 1/09* | (2006.01) |
| *C12M 1/06* | (2006.01) |
| *C12M 1/34* | (2006.01) |
| *B01F 3/04* | (2006.01) |

(52) U.S. Cl.
CPC .............. *C12M 41/42* (2013.01); *C12M 27/00* (2013.01); *B01F 2003/04631* (2013.01); *B01F 7/04* (2013.01); *C12M 23/28* (2013.01); *B01F 2003/04673* (2013.01); *B01F 7/22* (2013.01); *B01F 3/04531* (2013.01); *C12M 37/00* (2013.01); *B01F 7/00916* (2013.01); *C12M 23/56* (2013.01); *B01F 7/00183* (2013.01); *C12M 27/06* (2013.01); *B01F 7/00308* (2013.01)
USPC ............................................ 435/257.1; 47/1.4

(58) Field of Classification Search
USPC ................. 366/101; 435/302.1, 289.1, 295.2, 435/296.1, 257.1; 47/65.5
See application file for complete search history.

(56) References Cited

U.S. PATENT DOCUMENTS

| | | | | |
|---|---|---|---|---|
| 29,149 | A | * | 7/1860 | Durham .......................... 60/496 |
| 211,143 | A | * | 1/1879 | Pogarty .......................... 60/496 |

(Continued)

FOREIGN PATENT DOCUMENTS

| | | |
|---|---|---|
| EP | 0249433 A1 | 12/1987 |
| EP | 0617120 A2 | 9/1994 |

(Continued)

OTHER PUBLICATIONS

Supplementary European Search Report in co-pending European Patent Application No. 06850067.7, 6 pages (mailed Jul. 12, 2011).

(Continued)

*Primary Examiner* — Tony G Soohoo
(74) *Attorney, Agent, or Firm* — SoCal IP Law Group LLP; Guy Cumberbatch

(57) ABSTRACT

A pneumatic bioreactor includes a vessel containing a fluid to be mixed and at least one mixing device driven by gas pressure. A first embodiment includes a floating impeller that rises and falls in the fluid as gas bubbles carry it upward to the surface where the gas is then vented, permitting the impeller to sink in the fluid. The floating impeller may be tethered to a second impeller with a flexible member and pulley. The mixing speed is controlled with electromagnets in the vessel acting upon magnetic material in the impeller or its guides. In another embodiment, floating pistons mix the fluid, pushing it through a mixing plate with one or more apertures. In a third embodiment, the mixing device is a rotating drum with bubble-catching blades and rotating mixing plates with apertures. The top of the vessel for these mixers may include a closed top and sterile filters.

20 Claims, 13 Drawing Sheets

(56) References Cited

U.S. PATENT DOCUMENTS

| | | | |
|---|---|---|---|
| 257,505 A | 5/1882 | McMilan et al. | |
| 271,040 A | 1/1883 | Cook | |
| 272,656 A | 2/1883 | Cook | |
| 384,568 A | 6/1888 | Evans | |
| 650,063 A | 5/1900 | Kerten | |
| 2,098,962 A * | 11/1937 | Hellbach | 435/243 |
| 3,168,296 A | 2/1965 | Cowley | |
| 3,498,762 A | 3/1970 | Van Der Schee et al. | |
| 3,715,885 A | 2/1973 | Schur | |
| 3,722,185 A | 3/1973 | Miczek | |
| 3,786,781 A | 1/1974 | Poulsen | |
| 3,788,616 A | 1/1974 | Clough, Jr. | |
| 3,839,155 A * | 10/1974 | McAleer et al. | 435/298.2 |
| 3,886,074 A * | 5/1975 | Prosser | 210/150 |
| 3,911,064 A | 10/1975 | McWhirter et al. | |
| 3,930,816 A | 1/1976 | Miczek | |
| 3,969,446 A | 7/1976 | Franklin, Jr. | |
| 3,990,870 A | 11/1976 | Miczek | |
| 4,053,141 A | 10/1977 | Gussefeld | |
| 4,054,031 A | 10/1977 | Johnson | |
| 4,095,426 A | 6/1978 | Rhodes | |
| 4,101,384 A * | 7/1978 | Faust et al. | 435/298.1 |
| 4,160,736 A | 7/1979 | Prosser | |
| 4,170,114 A | 10/1979 | Pruett | |
| 4,196,590 A | 4/1980 | Fries | |
| 4,203,961 A | 5/1980 | Cowley | |
| 4,223,094 A * | 9/1980 | Vaseen | 435/298.2 |
| 4,245,473 A | 1/1981 | Sandoval | |
| 4,246,753 A | 1/1981 | Redmond | |
| 4,264,741 A * | 4/1981 | Friedman et al. | 435/298.2 |
| 4,266,402 A | 5/1981 | Pruett | |
| 4,268,385 A | 5/1981 | Yoshikawa | |
| 4,284,503 A * | 8/1981 | Stahler | 210/150 |
| 4,326,132 A | 4/1982 | Bokel | |
| 4,333,893 A * | 6/1982 | Clyde | 261/94 |
| 4,363,212 A | 12/1982 | Everett | |
| 4,416,546 A | 11/1983 | Parkins | |
| 4,540,491 A * | 9/1985 | Zimmer | 210/619 |
| 4,595,296 A | 6/1986 | Parks | |
| 4,655,603 A | 4/1987 | Palm | |
| 4,668,387 A * | 5/1987 | Davie et al. | 210/150 |
| 4,779,990 A | 10/1988 | Hjort | |
| 4,919,849 A | 4/1990 | Litz | |
| 4,944,598 A | 7/1990 | Steele | |
| 4,956,082 A * | 9/1990 | Choi | 210/150 |
| 5,075,234 A | 12/1991 | Tunac | |
| 5,081,035 A | 1/1992 | Halberstadt et al. | |
| 5,156,778 A | 10/1992 | Small | |
| 5,198,156 A | 3/1993 | Middleton | |
| 5,254,472 A * | 10/1993 | Brooks et al. | 435/290.2 |
| 5,326,459 A * | 7/1994 | Hlavach et al. | 210/150 |
| 5,570,517 A | 11/1996 | Luker | |
| 5,605,400 A | 2/1997 | Kojima | |
| 5,632,962 A | 5/1997 | Baker et al. | |
| 5,755,961 A | 5/1998 | Limcaco | |
| 5,755,976 A | 5/1998 | Kortmann | |
| 5,756,012 A | 5/1998 | McGlashan et al. | |
| 5,791,780 A | 8/1998 | Bakker | |
| 5,939,313 A | 8/1999 | Cheng | |
| 6,036,355 A | 3/2000 | Yant et al. | |
| 6,036,357 A | 3/2000 | Van Drie | |
| 6,135,629 A | 10/2000 | Dohmann | |
| 6,140,615 A | 10/2000 | Matsumoto | |
| 6,195,991 B1 | 3/2001 | De Shon | |
| 6,237,898 B1 | 5/2001 | Lafont | |
| 6,305,165 B1 | 10/2001 | Mizuki | |
| 6,322,056 B1 | 11/2001 | Drie | |
| 6,361,202 B1 | 3/2002 | Lee et al. | |
| 6,392,072 B1 | 5/2002 | Henriksen | |
| 6,406,624 B1 | 6/2002 | Devos | |
| 6,439,756 B1 | 8/2002 | Forschner et al. | |
| 6,447,243 B1 | 9/2002 | Kittle | |
| 6,599,426 B2 | 7/2003 | Van Drie | |
| 6,673,532 B2 | 1/2004 | Rao | |
| 6,926,437 B2 | 8/2005 | Van Drie | |
| 7,083,324 B2 | 8/2006 | Van Drie | |
| 7,083,720 B2 * | 8/2006 | Miller | 210/150 |
| 7,201,884 B2 | 4/2007 | Cohen | |
| 7,628,528 B2 * | 12/2009 | Zeikus | 366/102 |
| 7,663,259 B2 * | 2/2010 | Baarman et al. | 290/43 |
| 7,713,730 B2 * | 5/2010 | Zeikus et al. | 435/289.1 |
| 7,776,211 B2 * | 8/2010 | Limcaco | 210/150 |
| 7,819,576 B2 * | 10/2010 | Zeikus | 366/102 |
| 2001/0031491 A1 | 10/2001 | Curtis | |
| 2002/0110915 A1 | 8/2002 | Shaaltiel | |
| 2003/0161216 A1 | 8/2003 | Gigas et al. | |
| 2005/0158851 A1 | 7/2005 | Furey | |
| 2005/0201202 A1 | 9/2005 | Drie | |
| 2005/0258083 A1 * | 11/2005 | Miller | 210/150 |
| 2005/0272146 A1 | 12/2005 | Hodge et al. | |
| 2007/0091716 A1 | 4/2007 | Zeikus | |
| 2008/0135474 A1 * | 6/2008 | Limcaco | 210/602 |
| 2008/0206734 A1 * | 8/2008 | Asgari | 435/1.1 |
| 2008/0206862 A1 * | 8/2008 | Asgari | 435/325 |
| 2008/0261299 A1 | 10/2008 | Zeikus et al. | |
| 2008/0268530 A1 | 10/2008 | Zeikus et al. | |
| 2009/0230040 A1 * | 9/2009 | Limcaco | 210/151 |
| 2009/0269849 A1 | 10/2009 | Lee et al. | |
| 2010/0041095 A1 | 2/2010 | Zeikus | |
| 2010/0081122 A1 * | 4/2010 | Shibuya et al. | 435/3 |
| 2010/0276361 A1 * | 11/2010 | Limcaco | 210/602 |

FOREIGN PATENT DOCUMENTS

| | | |
|---|---|---|
| EP | 1120460 A1 | 8/2001 |
| JP | 60-164476 | 8/1985 |
| JP | 2005279383 A | 10/2005 |
| KR | 1020080077542 A | 8/2008 |
| WO | WO 2007/111677 A2 | 10/2007 |

OTHER PUBLICATIONS

Office Action in co-pending Japanese Patent Application No. JP2008-538145, 6 pages (mailed Aug. 2, 2011).

Office Action in co-pending U.S. Appl. No. 12/428,778, 32 pages (mailed Oct. 7, 2011).

Singapore (Australian) Cover Sheet, Search Report, Written Opinion, and Citation Annexes for corresponding Singapore Patent Application No. SG 200802702-1, 7 pages (mailed Apr. 28, 2009).

International Search Report and Written Opinion for PCT Patent Application No. PCT/US2006/060183, 6 pages (mailed Aug. 21, 2008).

International Preliminary Report on Patentability for PCT Patent Application No. PCT/US2006/060183, 5 pages (mailed Sep. 16, 2008).

International Search Report, and Written Opinion for PCT Patent Application No. PCT/US2008/005010, 15 pages (mailed May 15, 2009).

Examiner's First Report issued in co-pending Australian Application No. 2006340808, 3 pages (dated May 12, 2010).

First Office Action (English translation only) issued in co-pending Chinese Application No. 2006800394149, 5 pages (date not provided).

Second Office Action (English translation only) issued in co-pending Chinese Application No. 2006800394149, 4 pages (date not provided).

Decision of Rejection (English translation only) issued in co-pending Chinese Application No. 2006800394149, 3 pages (dated May 25, 2011).

Final Office Action in co-pending U.S. Appl. No. 12/428,778, 21 pages, (dated Aug. 22, 2012).

\* cited by examiner

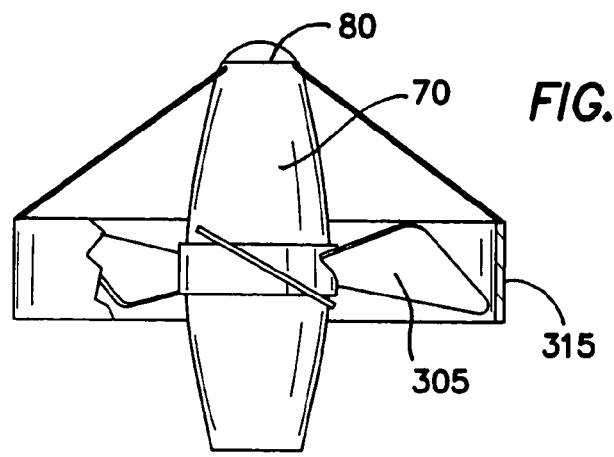
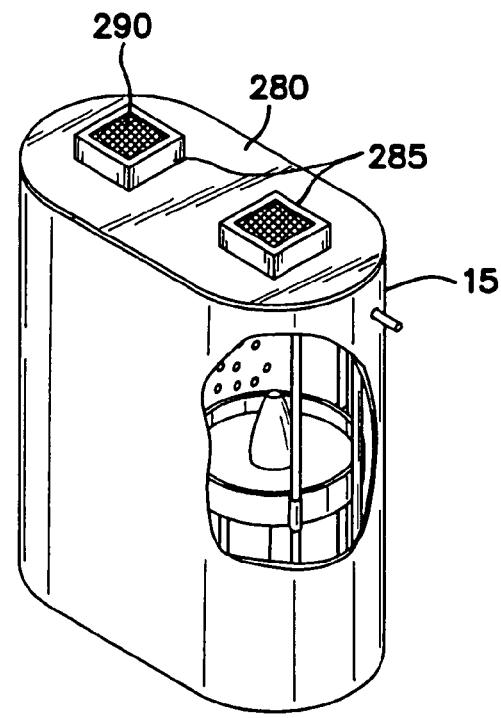
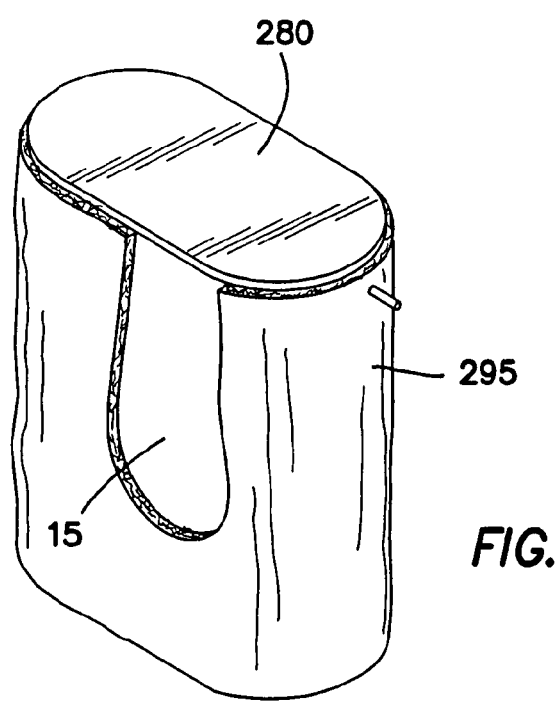

METHODS OF USING PNEUMATIC BIOREACTORS

CROSS-REFERENCE TO RELATED APPLICATION

This application is a continuation-in-part application claiming priority under 35 U.S.C. §120 of U.S. patent application Ser. No. 11/739,089 filed Apr. 23, 2007, now abandoned, and a continuation-in-part application claiming priority under 35 U.S.C. §120 of U.S. patent application Ser. No. 12/606,519 filed Oct. 27, 2009, now U.S. Pat. No. 7,819,576, which is a continuation application of U.S. patent application Ser. No. 11/258,742, filed Oct. 26, 2005, now U.S. Pat. No. 7,628,528, the respective disclosures of which are hereby incorporated by reference.

FIELD OF INVENTION

The invention pertains to apparatus for mixing solutions. More particularly, the invention relates to methods for using pneumatically operated mixers for use in closed, sterile environments.

BACKGROUND OF THE INVENTION

Efforts of biopharmaceutical companies to discover new biological drugs have increased exponentially during the past decade-and-a-half. Bioreactors have been used for cultivation of microbial organisms for production of various biological or chemical products in the pharmaceutical, beverage, and biotechnological industry. Most biological drugs are produced by cell culture or microbial fermentation processes which require sterile bioreactors and an aseptic culture environment. An increasing number of biological drug candidates are in development. Stringent testing, validation, and thorough documentation of process for each drug candidate are required by FDA to ensure consistency of the drug quality used for clinical trials to the market. However, shortages of global biomanufacturing capacity are anticipated in the foreseeable future, particularly as production needs will increase as such new drugs are introduced to the market.

A production bioreactor contains culture medium in a sterile environment that provides various nutrients required to support growth of the biological agents of interest. Stainless steel stir tanks have been the only option for large scale production of biological products in suspension culture. Manufacturing facilities with conventional stainless bioreactors, however, require large capital investments for construction, high maintenance costs, long lead times, and inflexibilities for changes in manufacturing schedules and production capacities. Conventional bioreactors use mechanically driven impellors to mix the liquid medium during cultivation. The bioreactors can be reused for the next batch of biological agents after cleaning and sterilization of the vessel. The procedure of cleaning and sterilization requires a significant amount of time and resources, especially to monitor and to validate each cleaning step prior to reuse for production of biopharmaceutical products. Due to the high cost of construction, maintenance and operation of the conventional bioreactors, single use bioreactor systems made of disposable plastic material have become an attractive alternative.

While several mixing methods of liquid in disposable bioreactors have been proposed in recent years, none of them provides efficient mixing for large scale (greater than 1000 liters) without expensive operating machinery. For this reason, a number of non-invasive and/or disposable mixing systems that do not require an external mechanical operation have been developed. Many of these systems work well within certain size ranges, however, problems sometimes arise as larger mixing systems are attempted.

Single use disposable bioreactor systems have been introduced to market as an alternative choice for biological product production. Such devices provide more flexibility on biological product manufacturing capacity and scheduling, avoid risking major upfront capital investment, and simplify the regulatory compliance requirements by eliminating the cleaning steps between batches. However, the mixing technology of the current disposable bioreactor system has limitations in terms of scalability to sizes beyond 200 liters and the expense of large scale units. Therefore, a disposable single use bioreactor system which is scalable beyond 1000 liters, simple to operate, and cost effective will be needed as a substitute for conventional stainless steel bioreactors for biopharmaceutical research, development, and manufacturing.

It is an objective of the present invention to provide a pneumatic bioreactor that is capable of efficiently and thoroughly mixing solutions without contamination. It is a further objective to such a reactor that can be scaled to relatively large sizes using the same technology. It is a still further objective of the invention to a bioreactor that can be produced in a disposable form. It is yet a further objective of the invention to provide a bioreactor that can be accurately controlled by internal pneumatic force, as to speed and mixing force applied to the solution without creating a foaming problem. Finally, it is an objective to provide a bioreactor that is simple and inexpensive to produce and to operate while fulfilling all of the described performance criteria.

SUMMARY OF THE INVENTION

A pneumatic bioreactor providing all of the desired features can be constructed from the following components. A containment vessel is provided. The vessel has a top, a closed bottom, a surrounding wall and is of sufficient size to contain a fluid to be mixed and a mixing apparatus. The mixing apparatus includes at least one gas supply line. The supply line terminates at an orifice adjacent the bottom of the vessel. At least one buoyancy-driven mixing device is provided. The mixing device moves in the fluid as gas from the supply line is introduced into and vented from the mixing device. When gas is introduced into the gas supply line the gas will enter the mixing device and cause the device to mix the fluid.

In a variant of the invention, the buoyancy-driven mixing device further includes at least one floating plunger. The plunger has a central, gas-holding chamber and a plurality of mixing elements located about the central chamber. The mixing elements are shaped to cause the plunger to agitate the fluid as the plunger rises in the fluid in the containment vessel. In a variant, the mixing elements are generally in the shape of a disc.

In yet another variant, the buoyancy-driven mixing device further includes at least one floating impeller, which is also provided as a mixing element. The impeller has the central, gas-containing chamber and a plurality of impeller blades arcurately located about the central chamber. The impeller blades are shaped to cause the impeller to revolve about a vertical axis as the impeller rises in fluid in the containment vessel.

The central chamber has a gas-venting valve. The valve permits escape of gas as the central chamber reaches a surface of the fluid. A constraining member is provided. The constraining member limits horizontal movement of the floating plunger and/or impeller ("plunger/impeller") as it rises or sinks in the fluid. When gas is introduced into the gas supply line, the gas will enter the gas-holding chamber and cause the floating plunger/impeller to rise by buoyancy in the fluid while agitating the fluid. When the gas-venting valve of the central chamber reaches the surface of the fluid, the gas will be released and the floating plunger/impeller will sink toward the bottom of the containment vessel where the central chamber will again be filled with gas, causing the floating plunger/impeller to rise.

In a further variant, a mixing partition is provided. The partition is located in the containment vessel adjacent the floating plunger/impeller and has at least one aperture to augment a mixing action of the floating plunger/impeller.

In another variant, means are provided for controlling a rate of assent of the floating plunger/impeller.

In still another variant, the means for controlling the rate of assent of the floating plunger/impeller includes a ferromagnetic substance attached to either of the floating plunger/impeller, the constraining member, or the outside housing, and a controllable electromagnet located adjacent the bottom of the containment vessel. The gas flow is interrupted by an on/off switch which is controlled by interactions of two magnetic substances. Therefore, the volume of gas supplied into the gas-holding chamber is determined by the strength of the electromagnetic power since the gas flow stops as the floating plunger/impeller starts to rise when the buoyancy becomes greater than the magnetic holding force.

In yet another variant, the central, gas-holding chamber further includes an opening. The opening is located at an upper end of the chamber. A vent cap is provided. The vent cap is sized and shaped to seal the opening when moved upwardly against it by buoyancy from gas from the supply line. A support bracket is provided. The support bracket is located within the chamber to support the vent cap when it is lowered after release of gas from the chamber. When the chamber rises to the surface of the fluid the vent cap will descend from its weight and the opening will permit the gas to escape, the chamber will then sink in the fluid and the vent cap will again rise due to buoyancy from a small amount of gas permanently enclosed in the vent cap, thereby sealing the opening.

In a further variant, a second floating plunger/impeller is provided. A second constraining member is provided, limiting horizontal movement of the second plunger/impeller as it rises in the fluid. At least one additional gas supply line is provided. The additional supply line terminates at an orifice adjacent the bottom of the vessel. At least one pulley is provided. The pulley is attached to the bottom of the containment vessel. A flexible member is provided. The flexible member attaches the chamber of the floating plunger to a chamber of the second floating plunger/impeller. The flexible member is of a length permitting the gas venting valve of the chamber of the floating plunger/impeller to reach the surface of the fluid while the chamber of the second floating plunger/impeller is spaced from the bottom of the containment vessel. When the floating plunger/impeller is propelled upwardly by buoyancy from the gas from the supply line the second floating plunger/impeller is pulled downwardly by the flexible member until the gas is released from the chamber of the floating plunger/impeller as its gas venting valve reaches the surface of the fluid. The chamber will then sink in the fluid as the second floating plunger/impeller rises by buoyancy from gas introduced from the second supply line.

In yet a further variant, the containment vessel is formed of resilient material, the material is sterilizable by gamma irradiation methods.

In still another variant, the pneumatic bioreactor further includes a cylindrical chamber. The chamber has an inner surface, an outer surface, a first end, a second end and a central axis. At least one mixing plate is provided. The mixing plate is attached to the inner surface of the chamber. First and second flanges are provided. The flanges are mounted to the cylindrical chamber at the first and second ends, respectively. First and second pivot points are provided. The pivot points are attached to the first and second flanges, respectively and to the containment vessel, thereby permitting the cylindrical chamber to rotate about the central axis. A plurality of gas-holding members are provided. The members extend from the first flange to the second flange along the outer surface of the cylindrical chamber and are sized and shaped to entrap gas bubbles from the at least one gas supply line. The gas supply line terminates adjacent the cylindrical chamber on a first side of the chamber below the gas-holding members. When gas is introduced into the containment vessel through the supply line it will rise in the fluid and gas bubbles will be entrapped by the gas-holding members. This will cause the cylindrical chamber to rotate on the pivot points in a first direction and the at least one mixing plate to agitate the fluid.

In yet another variant, a rate of rotation of the cylindrical chamber is controlled by varying a rate of introduction of gas into the gas supply line.

In a further variant, a second gas supply line is provided. The second supply line terminates adjacent the cylindrical chamber on a second, opposite side of the chamber below the gas holding members. Gas from the second supply line causes the cylindrical chamber to rotate on the pivot points in a second, opposite direction.

In still a further variant, the at least one mixing plate has at least one aperture to augment mixing of the fluid in the containment vessel.

In yet a further variant, the containment vessel further includes a closable top. The top has a vent, permitting the escape of gas from the gas supply line through a sterile filter.

In another variant of the invention, a temperature control jacket is provided. The jacket surrounds the containment vessel.

In a variant of the invention, an outside housing is provided. The housing is ring-shaped and surrounds the floating impeller and constrains its lateral movement. At least one supporting pole is provided. The pole extends from the bottom upwardly toward the top. The outside housing is slidably attached to the supporting pole. The floating impeller is rotatably attached to the outside housing.

In still another variant, the impeller blades are rotatably mounted to the central chamber and the central chamber is fixedly attached to the outside housing.

In a further variant, the impeller blades are fixedly mounted to the central chamber and rotatably mounted to the outside housing.

In still a further variant, the outside housing further includes a horizontal interior groove located on an inner surface of the housing. The impeller blades include a projection, sized and shaped to fit slidably within the groove.

In yet another variant, the vent cap further includes an enclosed gas cell. The cell causes the cap to float in the fluid and thereby to reseal the opening after the gas has been released when the chamber reached the surface of the fluid.

In a further variant, wherein the pneumatic bioreactor further includes a second floating impeller, a second outside housing surrounding the second floating impeller is provided. At least one additional supporting pole is provided. At least one additional gas supply line is provided. The additional supply line terminates at an orifice at the bottom of the vessel.

The second outside housing is slidably attached to the additional supporting pole. The second floating impeller is rotatably attached to the second outside housing. At least one pulley is provided. The pulley is attached to the bottom of the containment vessel.

An appreciation of the other aims and objectives of the present invention and an understanding of it may be achieved by referring to the accompanying drawings and the detailed description of a preferred embodiment.

BRIEF DESCRIPTION OF THE DRAWINGS

FIG. 4A is a side elevational view of the FIG. 2 embodiment of the floating impeller.

FIG. 14 is a perspective view of the FIG. 5 embodiment illustrating a closable top and sterile filters.

FIG. 15 is a perspective view of the FIG. 5 embodiment illustrating a temperature control jacket surrounding the vessel.

DETAILED DESCRIPTION OF THE INVENTION

Figure 1:
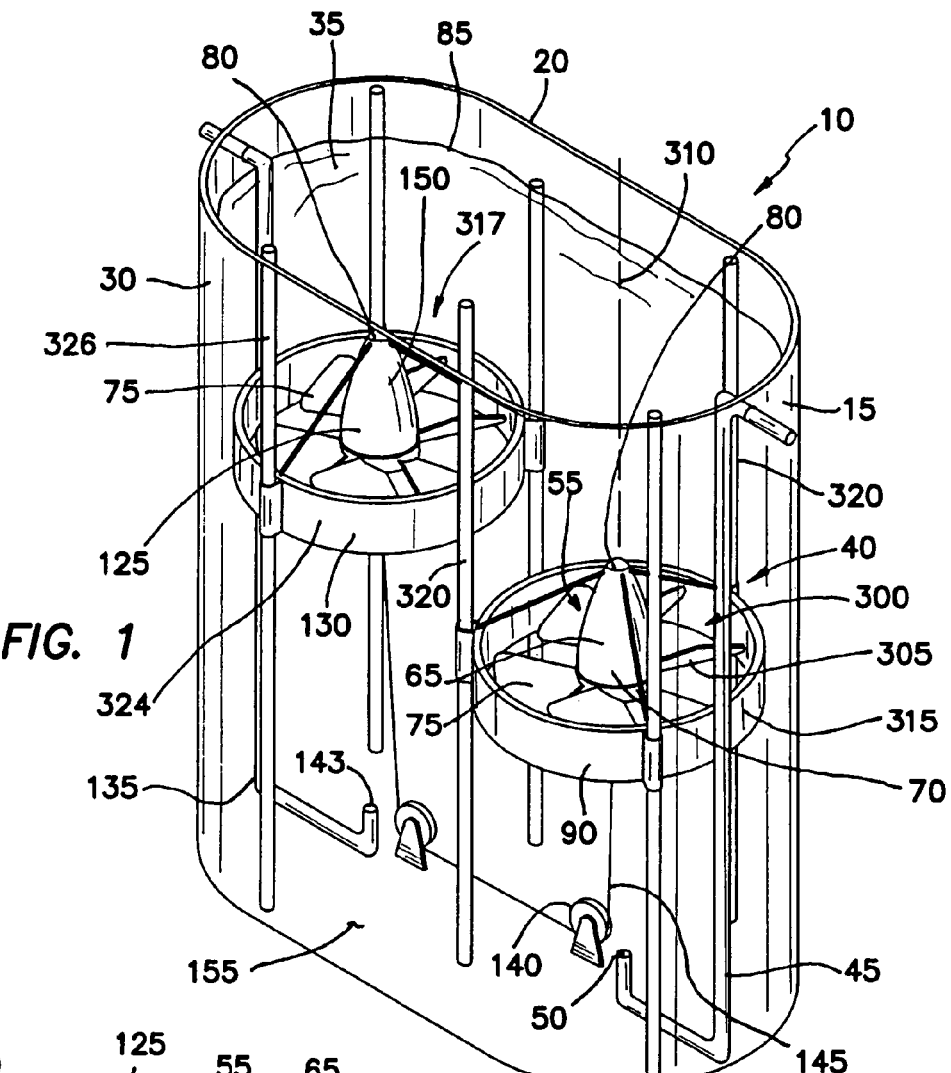
FIG. 1 is a perspective view of a first embodiment of the invention illustrating floating impellers and their control mechanisms.
Figure 2:
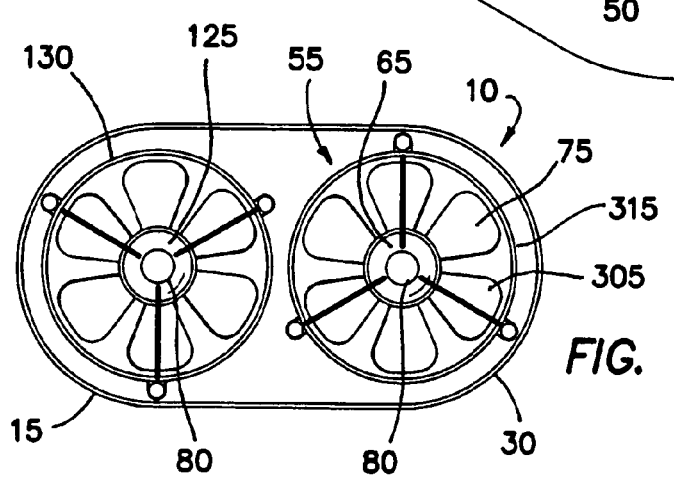
FIG. 2 is a top view of the FIG. 1 embodiment illustrating the floating chamber affixed to the constraining member with the impeller blades rotating upon the chamber.
Figure 3:
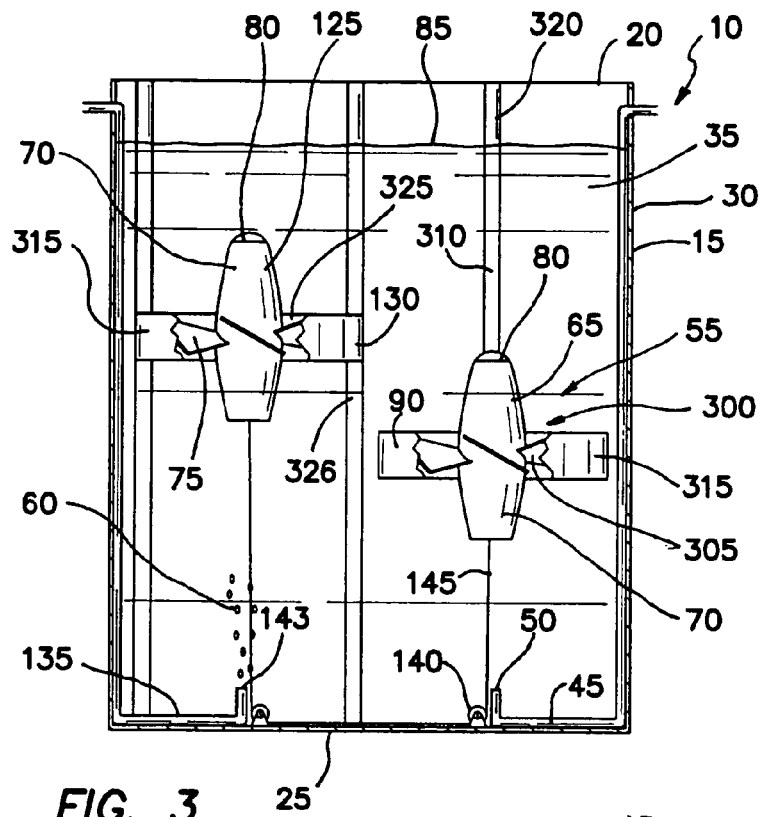
FIG. 3 is a side elevational view of the FIG. 1 embodiment.

A pneumatic bioreactor 10, as illustrated in FIGS. 1-3, providing all of the desired features can be constructed from the following components. A containment vessel 15 is provided. The vessel 15 has a top 20, a closed bottom 25, a surrounding wall 30 and is of sufficient size to contain a fluid 35 to be mixed and a mixing apparatus 40. The mixing apparatus 40 includes at least one gas supply line 45. The supply line 45 terminates at an orifice 50 adjacent the bottom 25 of the vessel 15. At least one buoyancy-driven mixing device 55 is provided. The mixing device 55 moves in the fluid 35 as gas 60 from the supply line 45 is introduced into and vented from the mixing device 55. When gas 60 is introduced into the gas supply line 45 the gas 60 will enter the mixing device 55 and cause the device to mix the fluid 35.

Figure 8:
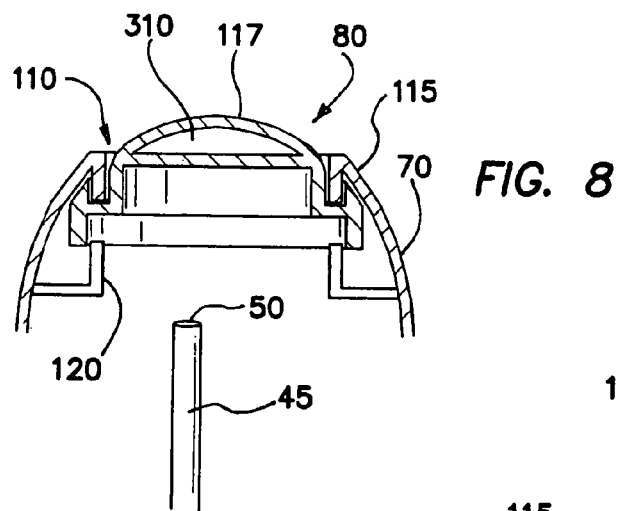
FIG. 8 is a cross-sectional side elevation of the floating chamber illustrating the vent cap in a closed position.
Figure 9:
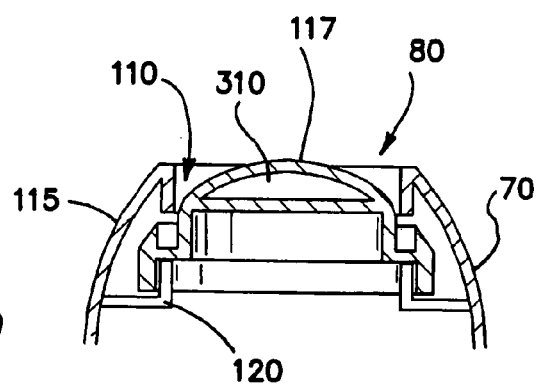
FIG. 9 is a cross-sectional side elevation of the floating chamber illustrating the vent cap in an open position.

In a variant of the invention, the buoyancy-driven mixing device 55 further includes at least one floating mixer 65. The mixer 65 has a central, gas-holding chamber 70 and a plurality of mixing elements 75 located about the central chamber 70. The mixing elements 75 are shaped to cause the mixer 65 to agitate the fluid 35 as the mixer 65 rises in the fluid 35 in the containment vessel 15. The central chamber 70, as illustrated in FIGS. 8 and 9, has a gas-venting valve 80. The valve 80 permits escape of gas 60 as the central chamber 70 reaches a surface 85 of the fluid 35. A constraining member 90 is provided. The constraining member 90 limits horizontal movement of the floating mixer 65 as it rises or sinks in the fluid 35. When gas 60 is introduced into the gas supply line 45, the gas 60 will enter the gas holding chamber 70 and cause the floating mixer 65 to rise by buoyancy in the fluid 35 while agitating the fluid 35. When the gas venting valve 80 of the central chamber 70 reaches the surface 85 of the fluid 35, the gas 60 will be released and the floating mixer 65 will sink toward the bottom 25 of the containment vessel 15 where the central chamber 70 will again be filled with gas 60, causing the floating mixer 65 to rise.

Figure 7:
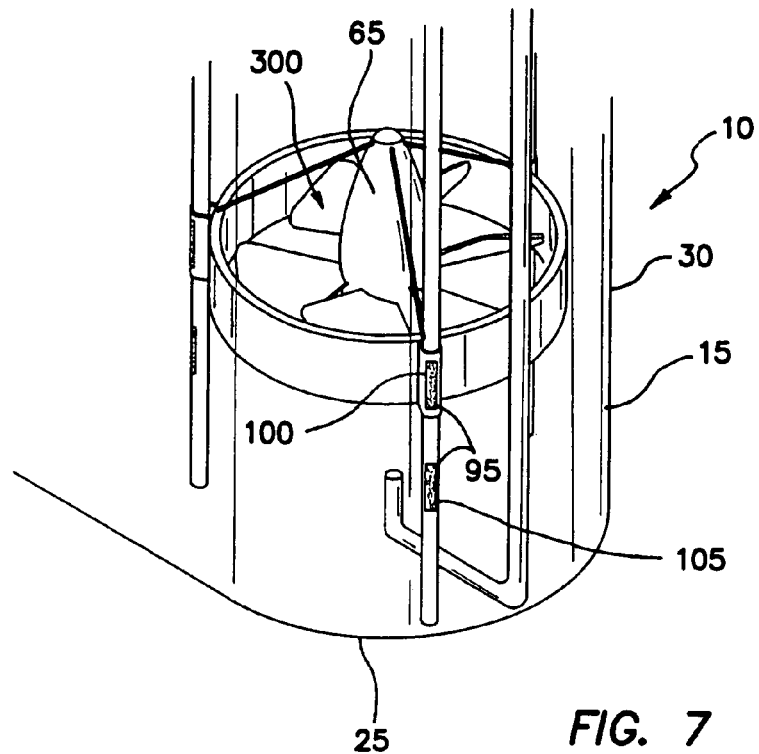
FIG. 7 is a perspective view of the gas supply line and magnetic assent control mechanism.

In another variant, means 95, as illustrated in FIG. 7, are provided for controlling a rate of assent of the floating mixer 65.

In still another variant, the means 95 for controlling the rate of assent of the floating mixer 65 includes a ferromagnetic substance 100 attached to either of the floating mixer 65 or the constraining member 90 and a controllable electromagnet 105 located adjacent the bottom 25 of the containment vessel 15.

In yet another variant, as illustrated in FIGS. 8 and 9, the central, gas-holding chamber 70 further includes an opening 110. The opening 110 is located at an upper end 115 of the chamber 70. A vent cap 117 is provided. The vent cap 117 is sized and shaped to seal the opening 110 when moved upwardly against it by buoyancy from gas 60 from the supply line 45. A support bracket 120 is provided. The support bracket 120 is located within the chamber 70 to support the vent cap 115 when it is lowered after release of gas 60 from the chamber 70. When the chamber 70 rises to the surface 85 of the fluid 35 the vent cap 115 will descend from its weight and the opening 110 will permit the gas 60 to escape, the chamber 70 will then sink in the fluid 35 and the vent cap 115 will again rise due to buoyancy from a small amount of gas 60 permanently enclosed in the vent cap 115, thereby sealing the opening 110.

In a further variant, as illustrated in FIGS. 1-3, a second floating mixer 125 is provided. A second constraining member 130 is provided, limiting horizontal movement of the second mixer 125 as it rises in the fluid 35. At least one additional gas supply line 135 is provided. The additional supply line 135 terminates at an orifice 143 adjacent the bottom 25 of the vessel 15. At least one pulley 140 is provided. The pulley 140 is attached to the bottom 25 of the containment vessel 15. A flexible member 145 is provided.

The flexible member 145 attaches the chamber 70 of the floating mixer 65 to a chamber 150 of the second floating mixer 125. The flexible member 145 is of a length permitting the gas venting valve 80 of the chamber 70 of the floating mixer 65 to reach the surface 85 of the fluid 35 while the chamber 70 of the second floating mixer 125 is spaced from the bottom 25 of the containment vessel 15. When the floating mixer 65 is propelled upwardly by buoyancy from the gas 60 from the supply line 45 the second floating mixer 125 is pulled downwardly by the flexible member 145 until the gas 60 is released from the chamber 70 of the floating mixer 65 as its gas venting valve 80 reaches the surface 85 of the fluid 35. The chamber 70 will then sink in the fluid 35 as the second floating mixer 125 rises by buoyancy from gas 60 introduced from the second supply line 135.

In yet a further variant, the containment vessel 15 is formed of resilient material 155, the material is sterilizable by gamma irradiation methods.

Figure 5:
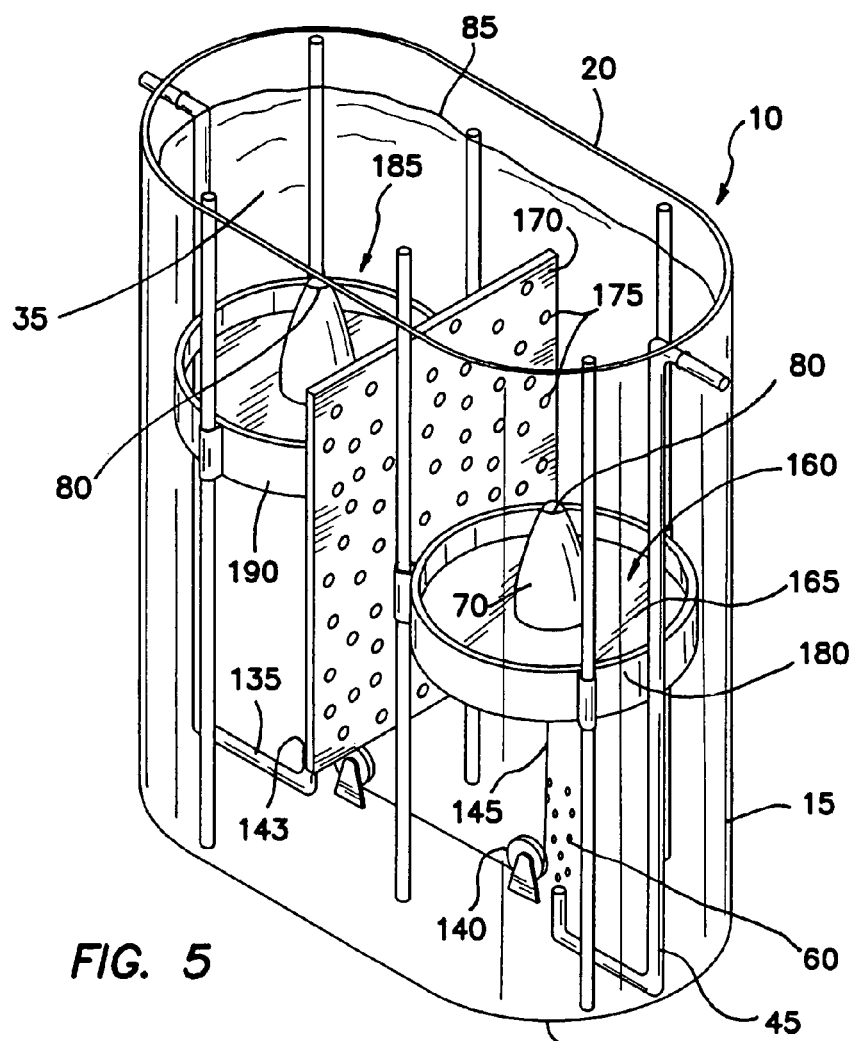
FIG. 5 is a perspective view of a second embodiment of the invention illustrating floating plungers and their control mechanisms.
Figure 6:
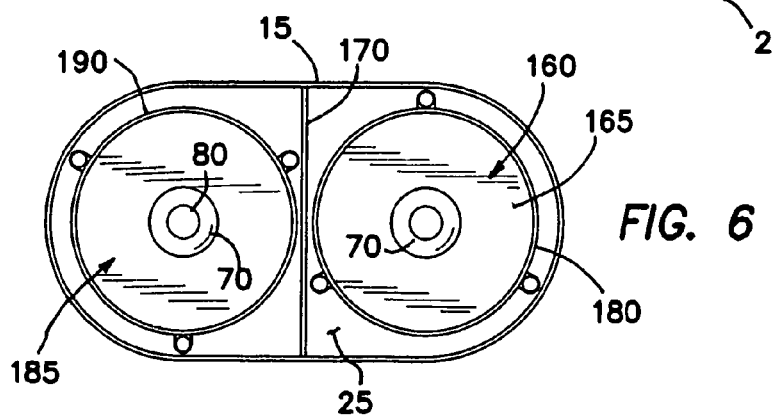
FIG. 6 is a top view of the FIG. 5 embodiment illustrating the floating plungers.

In still a further variant, as illustrated in FIGS. 5 and 6, the buoyancy-driven mixing device 10 further includes at least one floating plunger 160. The plunger 160 has a central, gas-holding chamber 70 and at least one disk 165 located about the central chamber 70. The disk 165 is shaped to cause the plunger 160 to agitate the fluid 35 as the plunger 160 rises in the fluid 35 in the containment vessel 15. The central chamber 70 has a gas-venting valve 80. The valve 80 permits escape of gas 60 as the central chamber 70 reaches a surface 85 of the fluid 35. A mixing partition 170 is provided. The partition 170 is located in the containment vessel 15 adjacent the floating plunger 160 and has at least one aperture 175 to augment a mixing action of the floating plunger 160. A constraining member 180 is provided. The constraining member 180 limits horizontal movement of the plunger 160 as it rises or sinks in the fluid 35. When gas 60 is introduced into the gas supply line 45 the gas 60 will enter the gas holding chamber 70 and cause the floating plunger 160 to rise by buoyancy in the fluid 35 while agitating the fluid 35. When the gas venting valve 80 of the central chamber 70 reaches the surface 85 of the fluid 35, the gas 60 will be released and the floating plunger 160 will sink toward the bottom 25 of the containment vessel 15 where the central chamber 70 will again be filled with gas 60, causing the floating plunger 160 to rise.

In another variant of the invention, a second floating plunger 185 is provided. A second constraining member 190 is provided, limiting horizontal movement of the second plunger 185 as it rises in the fluid 35. At least one additional gas supply line 135 is provided. The additional supply line 135 terminates at an orifice 143 adjacent the bottom 25 of the vessel 15. At least one pulley 140 is provided. The pulley 140 is attached to the bottom 25 of the containment vessel 15. A flexible member 145 is provided. The flexible member 145 attaches the chamber 70 of the floating plunger 160 to a chamber of the second floating plunger 185. The flexible member 145 is of a length permitting the gas venting valve 80 of the chamber 70 of the floating plunger 160 to reach the surface 85 of the fluid 35 while the chamber 70 of the second floating plunger 185 is spaced from the bottom 25 of the containment vessel 15. The mixing partition 170 is located between the floating plunger 160 and the second floating plunger 185. When the floating plunger 160 is propelled upwardly by buoyancy from the gas 60 from the supply line 45 the second floating plunger 185 is pulled downwardly by the flexible member 145 until the gas 60 is released from the chamber 70 of the floating plunger 160 as its gas venting valve 80 reaches the surface 85 of the fluid 30. The floating plunger 160 will then sink in the fluid 35 as the second floating plunger 185 rises by buoyancy from gas 60 introduced from the second supply line 135.

In still another variant, as illustrated in FIGS. 10-13, the pneumatic bioreactor 10 further includes a cylindrical chamber 195. The chamber 195 has an inner surface 200, an outer surface 205, a first end 210, a second end 215 and a central axis 220. At least one mixing plate 225 is provided. The mixing plate 225 is attached to the inner surface 200 of the chamber 195. First 230 and second 235 flanges are provided. The flanges 230, 235 are mounted to the cylindrical chamber 195 at the first 210 and second ends 215, respectively. First 240 and second 245 pivot points are provided. The pivot points 240, 245 are attached to the first 230 and second 235 flanges, respectively and to the containment vessel 15, thereby permitting the cylindrical chamber 195 to rotate about the central axis 220. A plurality of gas holding members 250 are provided. The members 250 extend from the first flange 230 to the second flange 235 along the outer surface 205 of the cylindrical chamber 195 and are sized and shaped to entrap gas bubbles 255 from the at least one gas supply line 45. The gas supply line 45 terminates adjacent the cylindrical chamber 195 on a first side 260 of the chamber 195 below the gas holding members 250. When gas 60 is introduced into the containment vessel 15 through the supply line 45 it will rise in the fluid 35 and gas bubbles 255 will be entrapped by the gas holding members 250. This will cause the cylindrical chamber 195 to rotate on the pivot points 240, 245 in a first direction 262 and the at least one mixing plate 225 to agitate the fluid 35.

In yet another variant, a rate of rotation of the cylindrical chamber 195 is controlled by varying a rate of introduction of gas 60 into the gas supply line 45.

Figure 12:
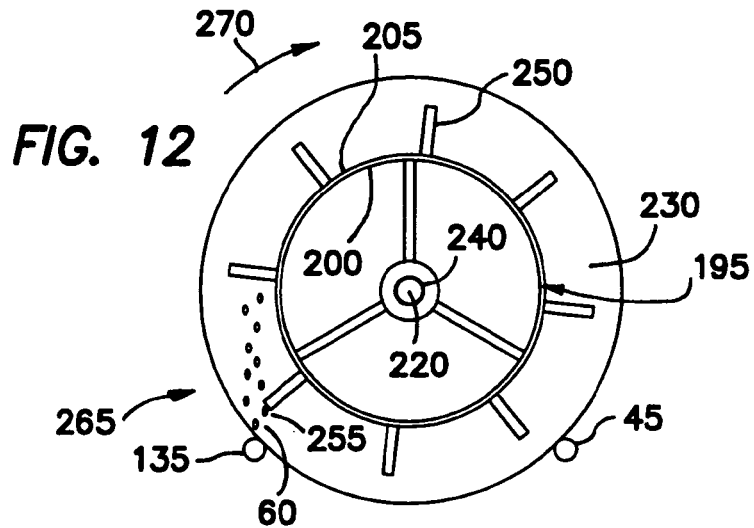
FIG. 12 is an end view of the FIG. 10 embodiment illustrating a pair of gas supply lines.

In a further variant, as illustrated in FIG. 12, a second gas supply line 135 is provided. The second supply line 135 terminates adjacent the cylindrical chamber 195 on a second, opposite side 265 of the chamber 195 below the gas holding members 250. Gas 60 from the second supply line 135 causes the cylindrical chamber 195 to rotate on the pivot points 240, 245 in a second, opposite direction 270.

Figure 10:
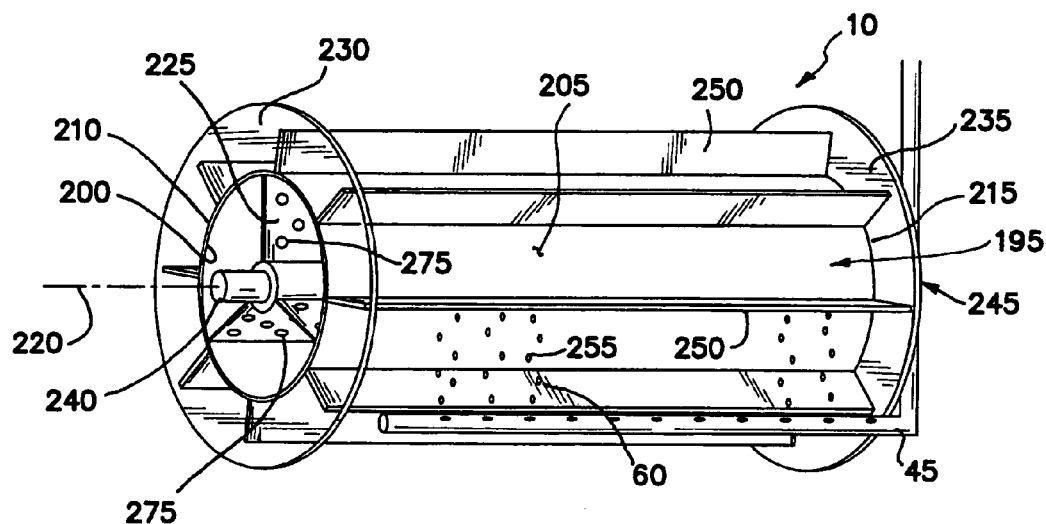
FIG. 10 is a perspective view of a third embodiment of the invention illustrating a rotating drum mixer with gas supply line.
Figure 11:
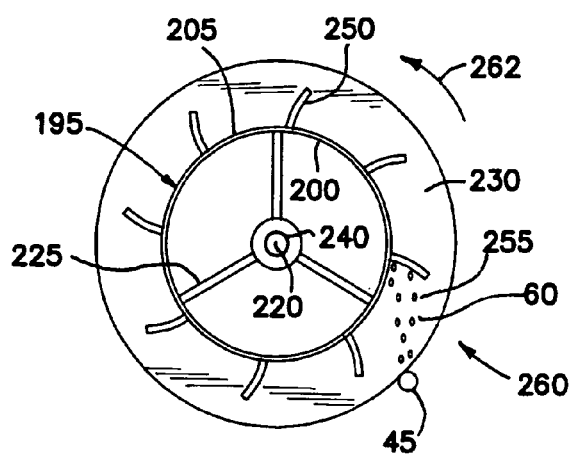
FIG. 11 is an end view of the FIG. 10 embodiment illustrating a single gas supply line.
Figure 13:
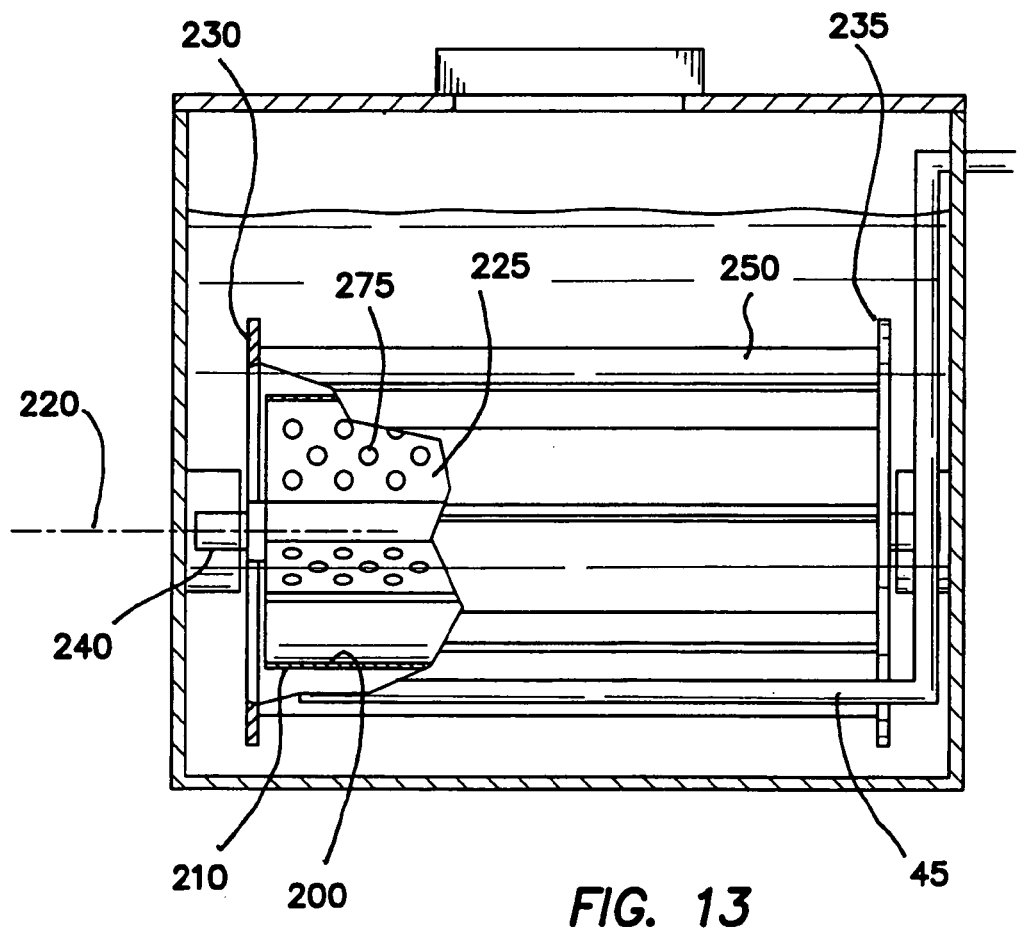
FIG. 13 is a side elevational view of the FIG. 10 embodiment illustrating a containment vessel.
Figure 16:
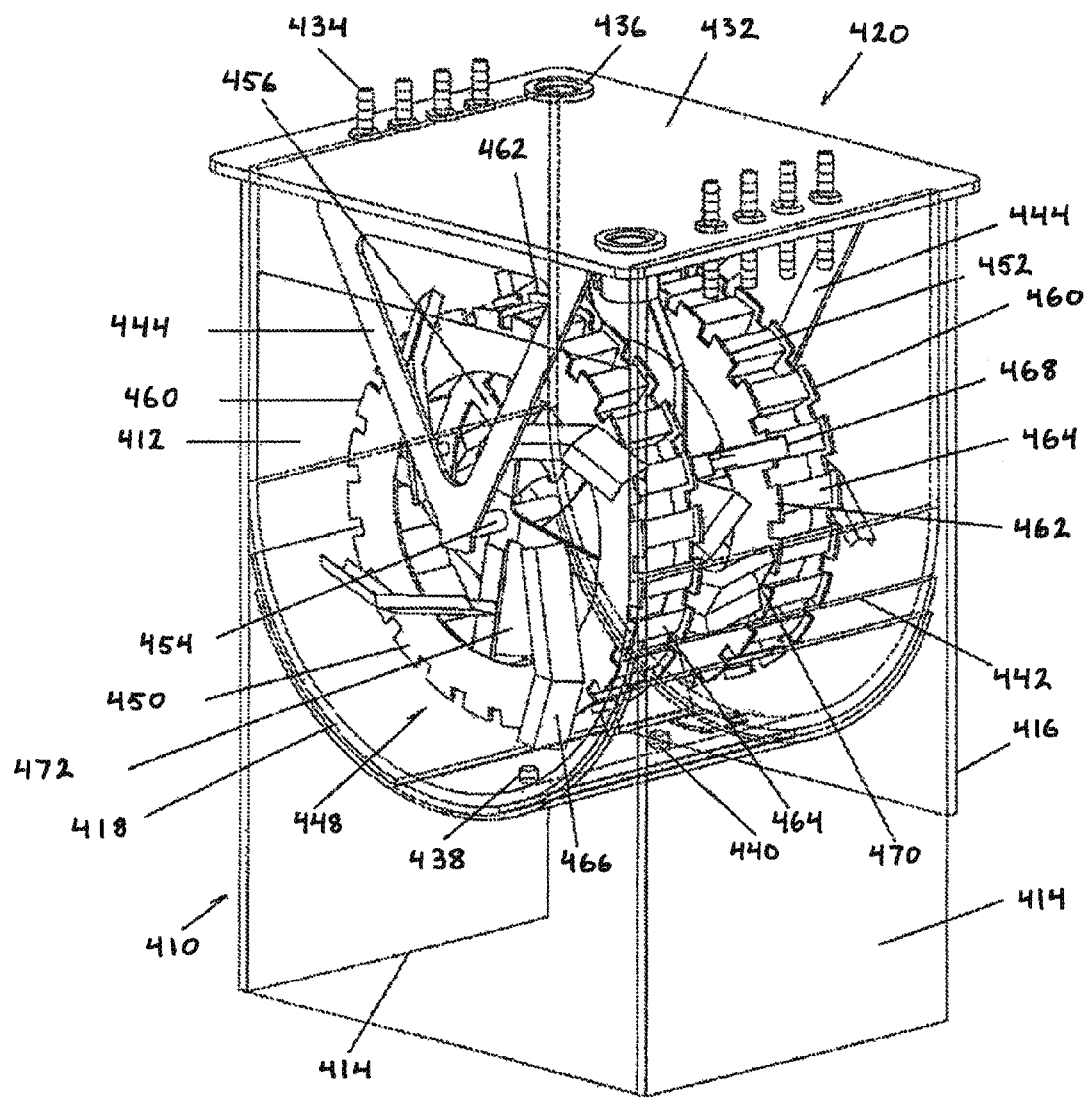
FIG. 16 is a perspective view of a pneumatic bioreactor shown through a transparent housing and containment vessel for clarity.

In still a further variant, as illustrated in FIGS. 10 and 13, the at least one mixing plate 225 has at least one aperture 275 to augment mixing of the fluid 35 in the containment vessel 15.

In yet a further variant, as illustrated in FIG. 14, the containment vessel 15 further includes a closable top 280. The top has a vent 285, permitting the escape of gas 60 from the gas supply line 45 through a sterile filter 290.

In another variant of the invention, as illustrated in FIG. 15, a temperature control jacket 295 is provided. The jacket 295 surrounds the containment vessel 15.

In yet another variant, as illustrated in FIGS. 1-3, a pneumatic bioreactor 10 includes a containment vessel 15. The vessel 15 has a top 20, a closed bottom 25, a surrounding wall 30 and is of sufficient size to contain a fluid 35 to be mixed and a mixing apparatus 40. The mixing apparatus 40 includes at least one gas supply line 45. The supply line 45 terminates at an orifice 50 at the bottom 25 of the vessel 15. At least one floating impeller 300 is provided. The impeller 300 has a central, gas-containing chamber 70 and a plurality of impeller blades 305 arcurately located about the central chamber 70. The impeller blades 305 are shaped to cause the impeller 300 to revolve about a vertical axis 310 as the impeller 300 rises in fluid 35 in the containment vessel 15.

The central chamber 70 has a gas-venting valve 80. The valve 80 permits escape of gas 60 as the central chamber 70 reaches a surface 85 of the fluid 35. An outside housing 315 is provided. The housing 315 is ring-shaped and surrounds the floating impeller 300 and constrains its lateral movement. At least one supporting pole 320 is provided. The pole 320 extends from the bottom 25 upwardly toward the top 20. The outside housing 315 is slidably attached to the supporting pole 320. The floating impeller 300 is rotatably attached to the outside housing 315. When gas 60 is introduced into the gas supply line 45 the gas 60 will enter the gas containing chamber 70 and cause the floating impeller 300 to rise in the fluid 35 while rotating and mixing the fluid 35. When the gas venting valve 80 of the central chamber 70 reaches the surface 85 of the fluid 35, the gas 60 will be released and the floating impeller 300 will sink toward the bottom 25 of the containment vessel 15 where the central chamber 70 will again be filled with gas 60, causing the floating impeller 300 to rise.

In still another variant, as illustrated in FIGS. 2 and 4A, the impeller blades 305 are rotatably mounted to the central chamber 70 and the central chamber 70 is fixedly attached to the outside housing 315.

Figure 2A:
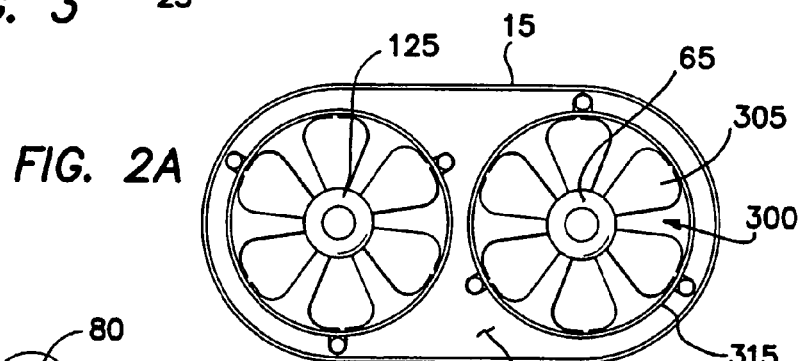
FIG. 2A is a top view of the FIG. 1 embodiment illustrating the floating chamber rotating within the constraining member with the impeller blades fixed to the chamber.
Figure 4:
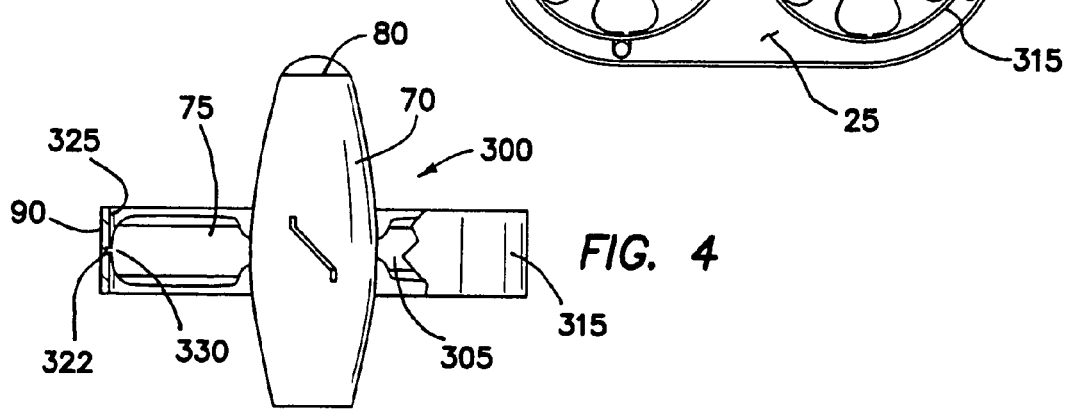
FIG. 4 is a side elevational view of the FIG. 2A embodiment of the floating impeller.

In a further variant, as illustrated in FIGS. 2A and 4, the impeller blades 305 are fixedly mounted to the central chamber 70 and rotatably mounted to the outside housing 315.

In still a further variant, the outside housing 315 further includes a horizontal interior groove 322 located on an inner surface 325 of the housing 315. The impeller blades 305 include a projection 330, sized and shaped to fit slidably within the groove 322.

In yet a further variant, as illustrated in FIG. 7, means 95 are provided for controlling a rate of assent of the floating impeller 300.

In another variant of the invention, the means 95 for controlling a rate of assent of the floating impeller 300 includes a ferromagnetic substance 100 attached to either the floating impeller 300 or the outside housing 315 and a controllable electromagnet 105 located adjacent the bottom 25 of the containment vessel 15.

In still another variant, as illustrated in FIGS. 8 and 9, the central, gas-containing chamber 70 further includes an opening 110 located at an upper end 115 of the chamber 70. A vent cap 115 is provided. The vent cap 115 is sized and shaped to seal the opening 110 when moved upwardly against it by pressure from gas 60 from the supply line 45. A support bracket 120 is provided. The support bracket 120 is located within the chamber 70 to support the vent cap 115 when it is lowered after release of gas 60 from the chamber 70. When the chamber 70 rises to the surface of the fluid 35 the vent cap 115 will descend from its weight and the opening 110 will permit the gas 60 to escape. The floating impeller 300 will then sink in the fluid 35 and the vent cap 115 will again rise due to pressure from gas 60 introduced into the chamber 70 from the gas line 45, thereby sealing the opening 110.

In yet another variant, the vent cap 115 further includes an enclosed gas cell 310. The cell 310 causes the cap 115 to float in the fluid 35 and thereby to reseal the opening 110 after the gas 60 has been released when the chamber 70 reached the surface 85 of the fluid 35.

In a further variant, as illustrated in FIGS. 1 and 3, the pneumatic bioreactor 10 further includes a second floating impeller 317. A second outside housing 324 surrounding the second floating impeller 317 is provided. At least one additional supporting pole 326 is provided. At least one additional gas supply line 135 is provided. The additional supply line 135 terminates at an orifice 143 at the bottom 25 of the vessel 15. The second outside housing 324 is slidably attached to the additional supporting pole 325. The second floating impeller 317 is rotatably attached to the second outside housing 324.

At least one pulley 140 is provided. The pulley 140 is attached to the bottom 25 of the containment vessel 15.

A flexible member 145 is provided. The flexible member 145 attaches the chamber 70 of the floating impeller 300 to a chamber 70 of the second floating impeller 317. The flexible member 145 is of a length to permit the gas venting valve 80 of the chamber 70 of the floating impeller 300 to reach the surface 85 of the fluid 35 while the chamber 70 of the second floating impeller 317 is spaced from the bottom 25 of the containment vessel 15. When the floating impeller 300 is propelled upwardly by pressure from the gas 60 from the supply line 45 the second floating impeller 315 will be pulled downwardly by the flexible member 145 until the gas 60 is released from the chamber 70 of the floating impeller 300 as its gas venting valve 80 reaches the surface 85 of the fluid 35, the floating impeller 300 will then sink in the fluid 35 as the second floating impeller 315 rises under pressure from gas 60 introduced from the second supply line 135.

FIGS. 16 through 20 illustrate a bioreactor positioned in a housing, generally designated 410. The housing 410 is structural and preferably made of stainless steel to include a housing front 412, housing sides 414 and a housing back 416. The housing back 416 does not extend fully to the floor or other support in order that access may be had to the underside of the bioreactor. The housing 410 includes a housing bottom 418 which extends from the housing sides 414 in a semi-cylindrical curve above the base of the housing 410. One of the front 412 or back 416 may act as a door to facilitate access to the interior of the housing 410.

Figure 17:
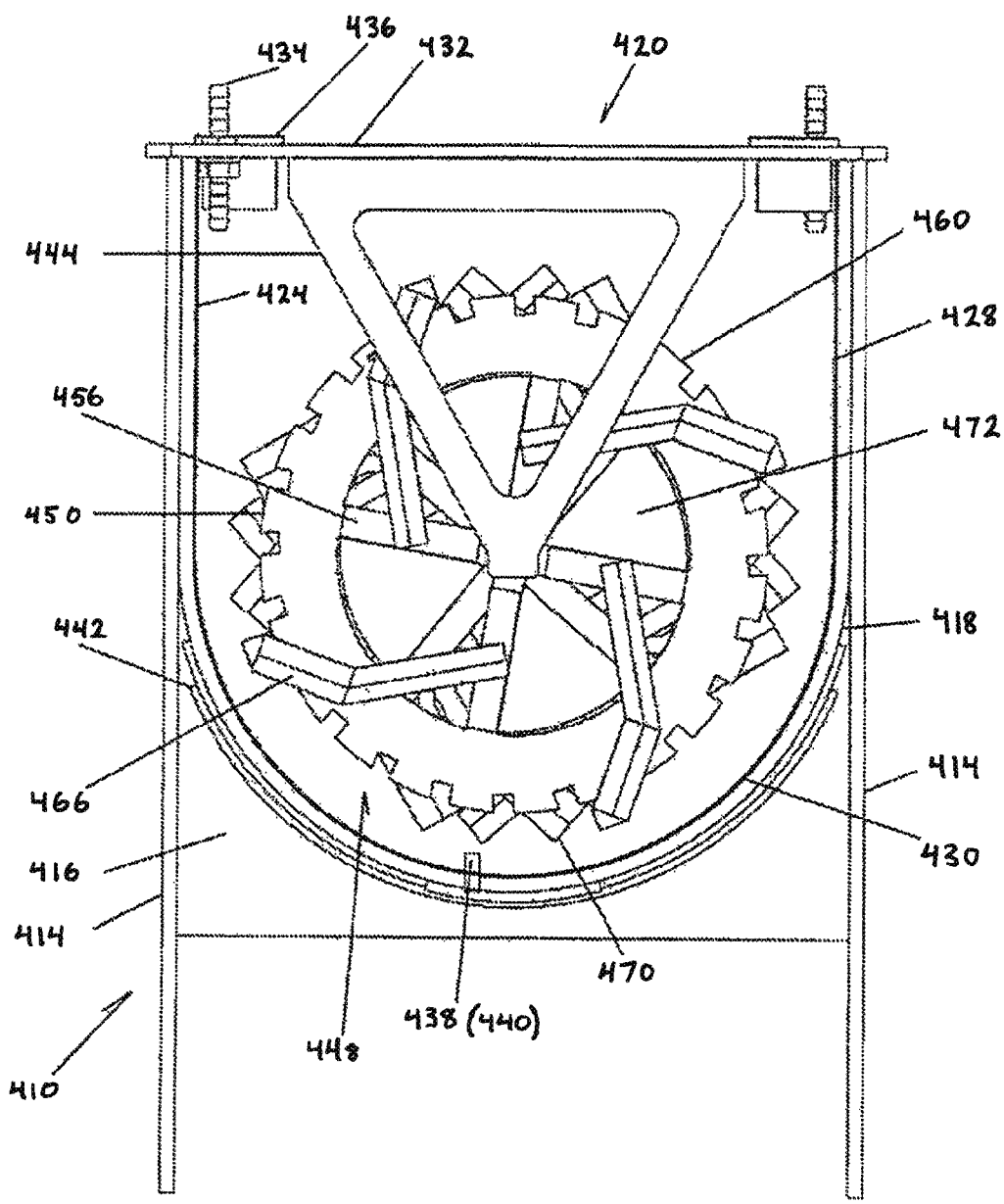
FIG. 17 is a front view of the pneumatic bioreactor of FIG. 16.
Figure 18:
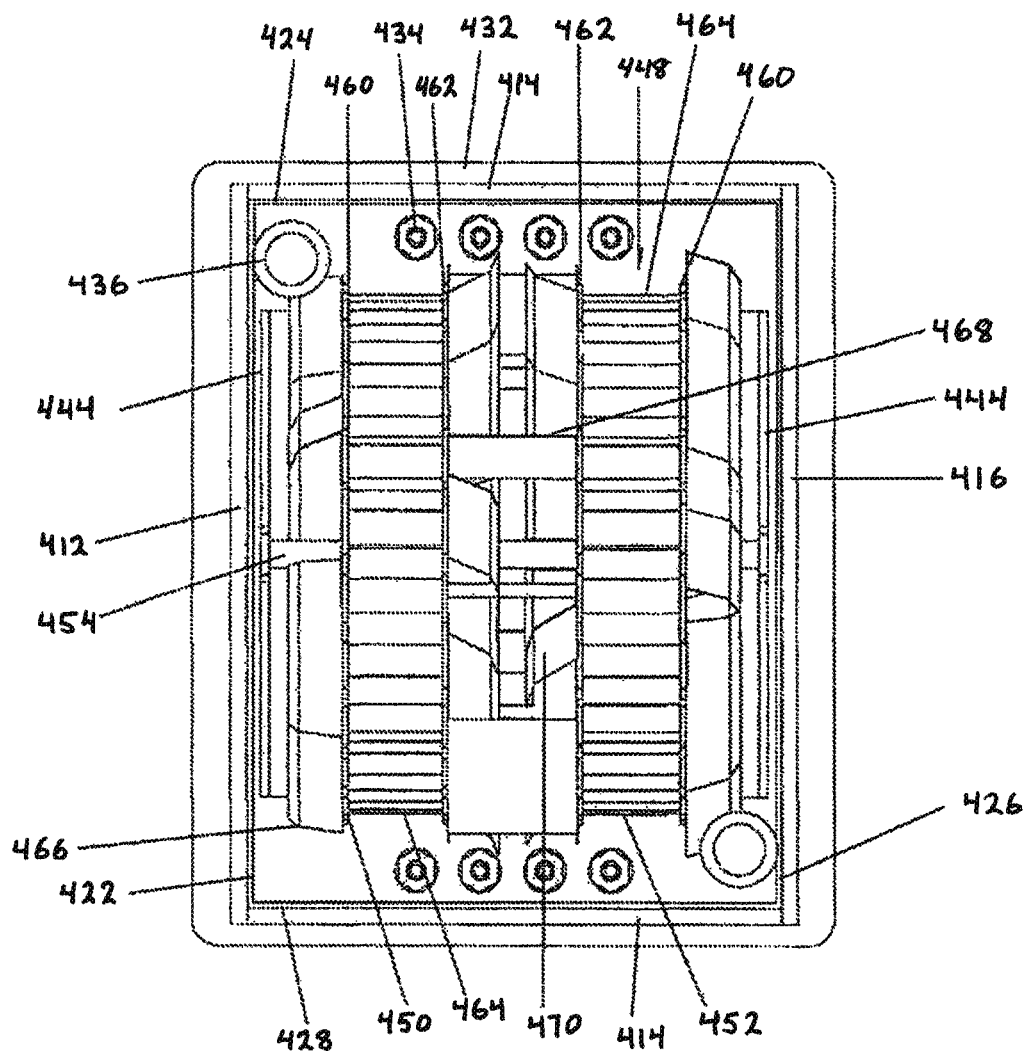
FIG. 18 is top view of the pneumatic bioreactor of FIG. 16.
Figure 19:
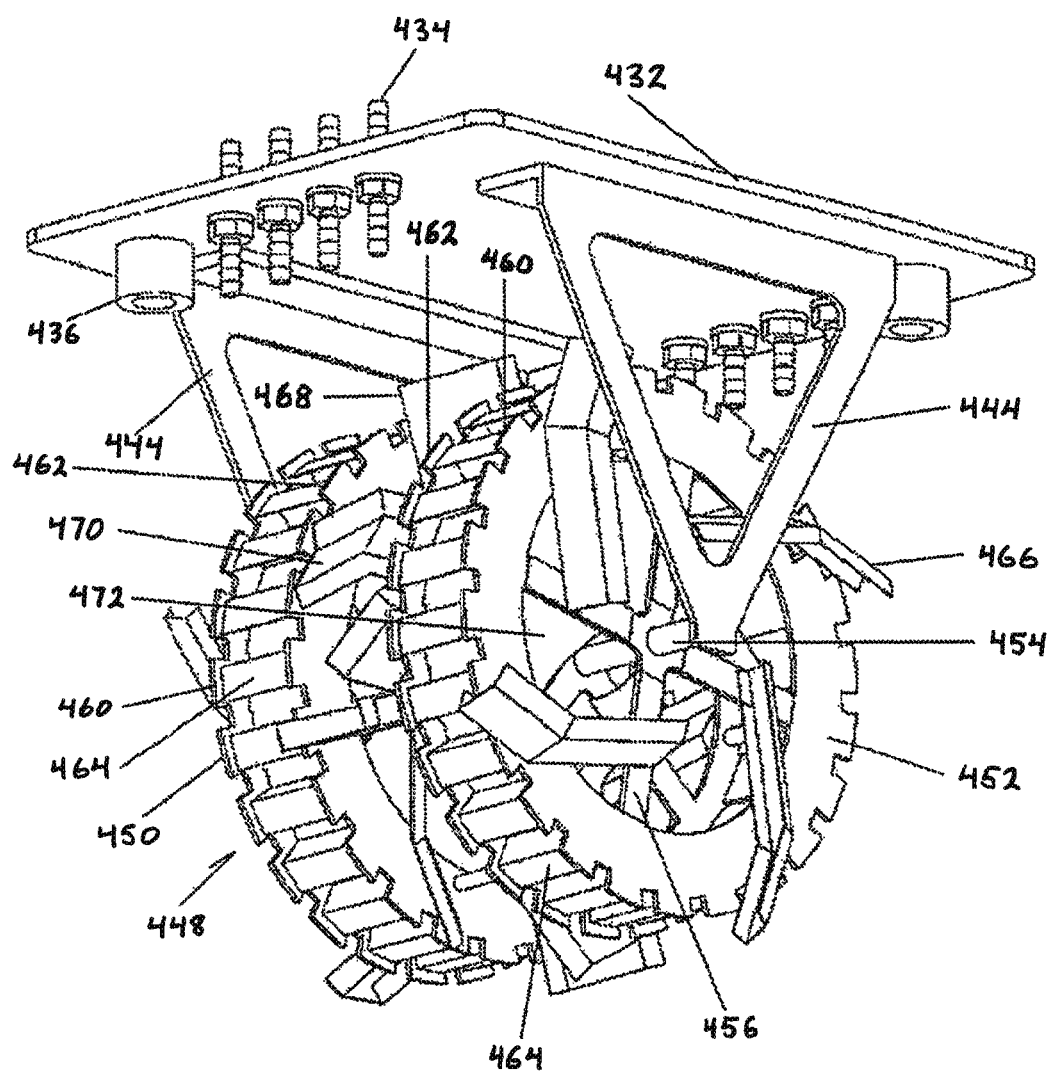
FIG. 19 is a perspective view of the top and mixing apparatus of the pneumatic bioreactor of FIG. 16.

The bioreactor includes a containment vessel, generally designated 420, defined by four vessel sides 422, 424, 426, 428, a semi-cylindrical vessel bottom 430, seen in FIG. 17, and a vessel top 432. Two of the vessel sides 424, 428 which are opposed each include a semicircular end. The other two vessel sides 422, 426 join with the semi-cylindrical vessel bottom 430 to form a continuous cavity between the two vessel sides 424, 428. All four vessel sides 422, 424, 426, 428 extend to and are sealed with the vessel top 432 to form a sealed enclosure. The vessel top 432 extends outwardly of the four vessel sides 422, 424, 426, 428 so as to rest on the upper edges of the structural housing front 412, sides 414 and back 416. Thus, the containment vessel 420 hangs from the top 432 in the housing 410. The vessel, with the exception of the vessel top 432, is of thin wall film which is not structural in nature. Therefore, the housing front 412, sides 414, back 416 and bottom 418 structurally support the containment vessel 420 depending from the vessel top 432 when filled with liquid. All joints of the containment vessel 420 are welded or otherwise sealed to provide the appropriate sealed enclosure which can be sterilized and closed ready for use.

The vessel top 432 includes access ports 434 for receipt or extraction of liquids, gases and powders and grains of solid materials. The access ports 436 in the vessel top 432 provide for receipt of sensors to observe the process. Two orifices 438, 440 are shown at the vessel bottom 430 slightly offset from the centerline to receive propellant gas for driving the rotational mixer as will be discussed below. The semi-cylindrical vessel bottom 430 defining a semi-cylindrical concavity within the containment vessel 420 also includes a temperature control sheet 442 which may include a heater with heating elements, a cooler with cooling coils, or both as may be employed to raise or lower the temperature of the contents of the containment vessel 420 during use. Sealed within the enclosure defining the containment vessel 420, struts 444 extend downwardly from the vessel top 432 to define a horizontal mounting axis at or close to the axis of curvature defined by the semi-cylindrical bottom 430.

A mixing apparatus includes a rotatably mounted rotational mixer, generally designated 448. The rotational mixer 448 is a general assembly of a number of functional components. The structure of the rotational mixer 448 includes two parallel wheels 450, 452 which are displaced from one another. These wheels are tied to an axle 454 by spokes 456. Additional stabilizing bars parallel to the axle 54 may be used to rigidify the rotational mixer 448.

Each wheel 450, 452 is defined by two parallel plates 460, 462. These plates 460, 462 include buoyancy-driven mixing cavities 464 there between. These cavities 464 operate to entrap gas supplied from below the wheels 450, 452 through the gas supply at orifices 438, 440. The orifices 438, 440 are offset from being directly aligned with the horizontal axis of rotation to insure that the buoyancy-driven cavities 464 are adequately filled with gas to power the rotational mixer 448 in rotation. In the embodiment of FIGS. 16 through 20, the buoyancy-driven cavity 464 in each one of the wheels 450, 452 are similarly oriented to receive gas from the orifices 438, 440 at the same time.

Outer paddles 466 are equiangularly placed to extend axially outwardly from the outer parallel plates 460 where they are attached. These outer paddles 466 can mix the liquid between the rotational mixer 448 and either side 424, 428. The outer paddles 466 are formed in this embodiment with a concavity toward the direction of rotation of the rotational mixer 448 and are inclined toward the direction of rotation as well such that they are disposed to induce flow entrained with constituents of the mix in the vessel inwardly toward the axis for flow through each wheel 450, 452 with the rotation of the rotational mixer 448. The outer paddles 466 may exhibit an inclined orientation on each of the outer parallel plates 460 such that any induced axial flow through each wheel 450, 452 will flow toward the center of the rotational mixer 448 in opposite directions. The number of outer paddles 466 may be increased from the four shown, particularly when the constituents of the mix in the vessel are not easily maintained in suspension. The outer paddles 466 may extend close to the vessel bottom 430 to entrain constituents of the mix in the vessel which may otherwise accumulate on the bottom. Such extensions beyond the wheels 450, 452 preferably do not inhibit rotation of the rotational mixer 448 through actual or close interaction with the vessel wall.

Figure 20:
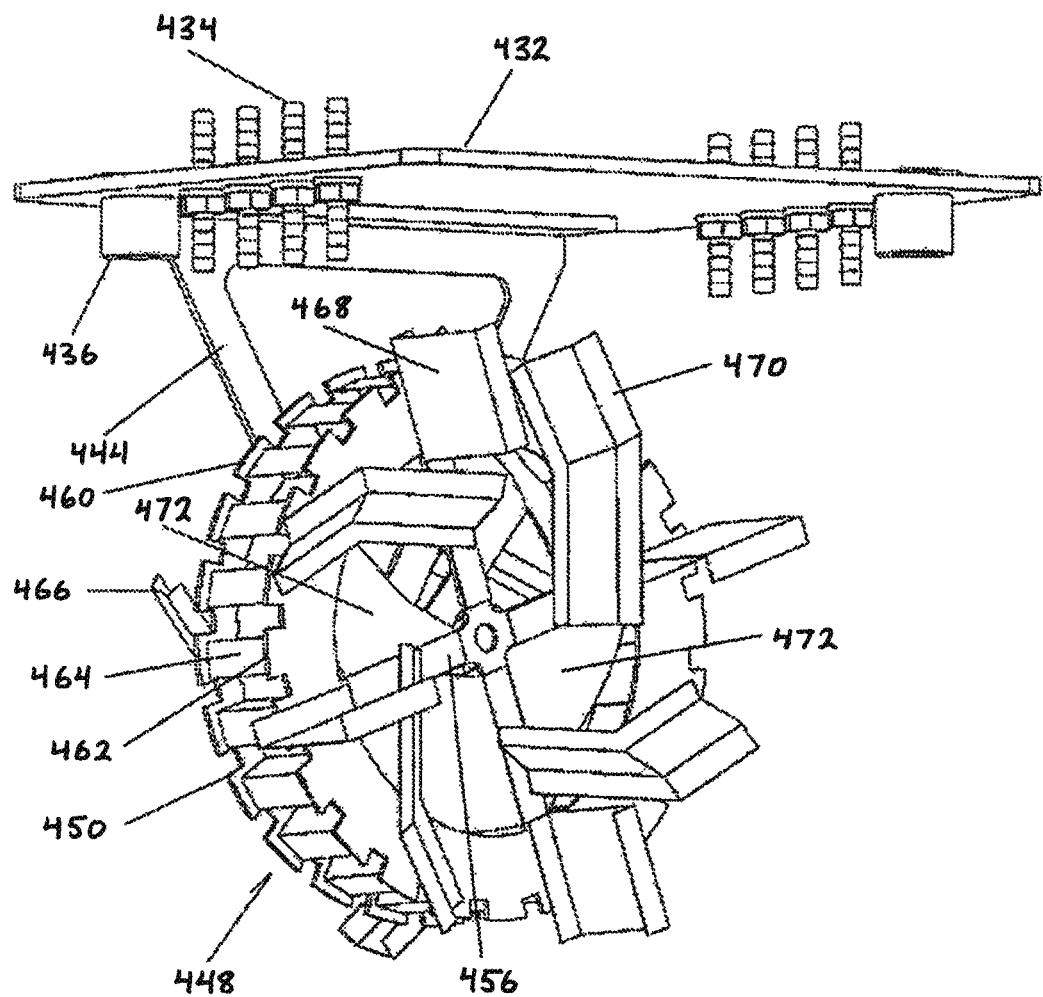
FIG. 20 is a perspective view of one wheel of the pneumatic bioreactor of FIG. 16.

Inwardly of the two wheels 450, 452, vanes 468 may be employed in some embodiments as can best be seen in FIG. 20. These vanes 468 extend axially inwardly from the inner parallel plates 462 to span the distance there between. The vanes 468 can also extend to induce flow radially outwardly from the rotational mixer 448 and beyond the rotational mixer 448 so as to impact and mix liquid outwardly of the rotational mixer. As with the outer paddles 466, the vanes 468 can be used to entrain constituents that tend to fall and collect on the vessel bottom 430. These vanes 468 may, in some instances not be preferred because of flow resistance or disruption of circulating flow. Empirical analysis is necessary in this regard depending on such things as rotational mixer speed, liquid viscosity, space to the vessel walls and the like. Four vanes 468 are illustrated on each wheel 450, 452 but the number can, as with the outer paddles 466, be increased or decreased with the performance of the mix.

Inner paddles 470 also extend axially inwardly from the inner parallel plates 462. These inner paddles 470 are convex facing toward the rotational direction and are inclined to draw flow axially through the wheels 450, 452. The inner paddles 470 can enhance radially outward flow with rotation of the rotational mixer 448 as well at the location shown inside of the wheels 450, 452. There can be any practical number of inner paddles 470, four being shown. Such paddles 470, if configured to extend past the perimeter of the wheels 450, 452, can urge flow off of the bottom as well and direct that flow axially outwardly to either side.

Located inwardly of each wheel 450, 452 is an impeller having blades 472. The two impellers provide principal axial thrust to the flow through the wheels 450, 452. The thrust resulting from these blades 472 both flow inwardly toward one another in this embodiment. This is advantageous in creating toroidal flow about the wheels and balance forces which would otherwise be imposed on the mountings. The placement of the blades 472 may be at other axial locations such as at either of the plates 460, 462. Where the impellers act alone, the blades 472 can be located anywhere from exterior of to interior to the rotational mixer with appropriate reconfiguration in keeping with slow speed impeller practice.

The mixing apparatus defined principally by the rotating rotational mixer 448 is positioned in the containment vessel 420 such that it extends into the semi-cylindrical concavity defined by the vessel bottom 430 and is sized, with the outer paddles 466, vanes 468 and inner paddles 470, to fill the concavity but for sufficient space between the mixing apparatus and the vessel sides 424, 428 and bottom 430 to avoid inhibiting free rotation of the rotational mixer 448. In one embodiment, the full extent of the mixing apparatus 426 is on the order of 10% smaller than the width of the cavity in the containment vessel 420 and about the same ratio for the diameter of the rotational mixer 448 to the semi-cylindrical vessel bottom 430. This spacing is not critical so long as the mixing apparatus is close enough and with commensurate speed to effect mixing throughout the concavity. Obviously, empirical testing is again of value. The liquid preferably does not extend above the mixing apparatus and the volume above the rotational mixer 448 will naturally be mixed as well.

In operation, the liquid, nutrients and active elements are introduced into the containment vessel 420 through the ports 434, 436. The level of material in the vessel 420 is below the top of the rotational mixer 448 to avoid the release of driving gas under the liquid surface which may cause foam. Gas is injected through the orifices 438, 440 to become entrapped in the buoyancy-driven cavity 464 in the rotational mixer 448. This action drives the rotational mixer 448 in a direction which is seen as clockwise in FIG. 17.

The blades 472 act to circulate the liquid within the containment vessel 420 with toroidal flow in opposite directions through the wheels 450, 452, radially outwardly from between the wheels 450, 452 and then radially inwardly on the outsides of the rotational mixer 448 to again be drawn into the interior of the rotational mixer 448. Mixing with turbulence is desired and the outer paddles 466, the vanes 468 and the inner paddles 470 contribute to the mixing and to the toroidal flow about each of the wheels 450, 452. The target speed of rotation is on the order of up to the low tens of rpm to achieve the similar mixing results as prior devices at 50 to 300 rpm. The difference may reduce shear damage in more sensitive materials. Oxygen may be introduced in a conventional manner as well as part of the driving gas to be mixed fully throughout the vessel 420 under the influence of the mixing apparatus.

Figure 21:
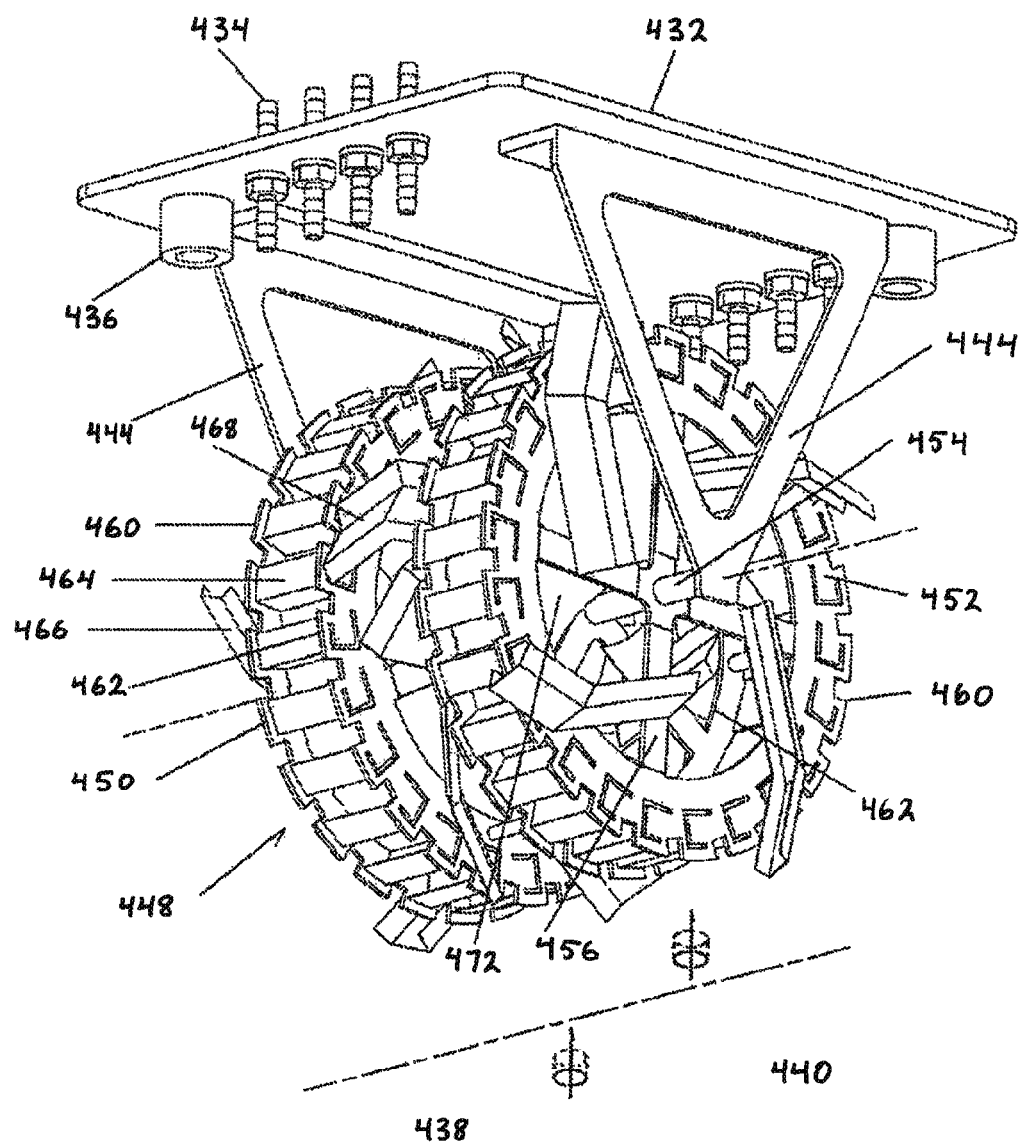
FIG. 21 is a perspective view of the top and mixing apparatus of a modified bioreactor of FIG. 16.

FIG. 21 illustrates a variation on the embodiment of FIGS. 16 through 20. In this embodiment, the buoyancy-driven mixing cavities 464 are reversed in one of the wheels 450, 452 for driving in the opposite direction. Similarly, the orifices 438, 440 are offset to either side of the horizontal axis of rotation. The gas through the orifices 438, 440 is independently controlled to allow selection of rotation of the rotational mixer in either direction.

Thus, an improved pneumatic bioreactor is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

An appreciation of the other aims and objectives of the present invention and an understanding of it may be achieved by referring to the accompanying drawings and the detailed description of a preferred embodiment.

The invention claimed is:

1. A method of growing a biological agent within a single use bioreactor, the method comprising the steps of:
   providing a containment vessel for holding biological contents, the containment vessel comprising a generally rectangular upper portion in horizontal section and a semi-cylindrical lower portion defining a semi-cylindrical concavity therewithin;
   providing a rotatable buoyancy-driven mixing device located within the containment vessel and having a substantially horizontal axis of rotation, the mixing device having a diameter such that when it rotates it substantially fills the semi-cylindrical concavity;
   sterilizing the containment vessel and the mixing device so that at least the interior of the containment vessel and the mixing device are sterile;
   providing a culture medium within the containment vessel;
   providing nutrients within the containment vessel to support growth of the biological agent within the culture medium;
   enclosing the containment vessel such that the culture medium is not exposed to the surrounding environment;
   rotating the mixing device about said horizontal axis to mix the contents of the containment vessel by introducing gas into the containment vessel at a location below the mixing device such that at least a portion of the gas rising within the containment vessel is temporarily captured by a portion of the mixing device to cause rotation of the mixing device due to the buoyancy of the captured gas; and discarding the containment vessel and mixing device after a single use of growing a biological agent.

2. The method of claim 1, further comprising controlling the temperature of the interior of the containment vessel to support growth of the biological agent.

3. The method of claim 1, further comprising controlling the speed of rotation of the mixing device by controlling the rate of introduction of gas into the containment vessel.

4. The method of claim 1, further comprising controlling the direction of rotation of the mixing device by introducing gas into the containment vessel below one side or the opposite side of the mixing device.

5. The method of claim 1, wherein said sterilizing step comprises sterilizing the containment vessel and the mixing device by gamma irradiation.

6. The method of claim 1, further including a rigid housing into which the containment vessel fits, the housing defining a semi-cylindrical lower section and the lower portion of the containment vessel being formed of a material that is non-structural such that the semi-cylindrical lower section of the housing structurally supports the lower portion of the containment vessel.

7. The method of claim 6, wherein a vessel top extends outwardly of containment vessel sides and rests on upper edges of the housing so as to suspend the containment vessel within the housing.

8. The method of claim 6, wherein the containment vessel is primarily formed of a thin wall film that is non-structural.

9. The method of claim 1, further including an impeller defined within an outer wheel on the mixing element configured to generate axial flow of at least a portion of the contents of the containment vessel upon rotation of the mixing device.

10. A method for performing a cell culture growth process comprising:

holding a cell culture medium within a single use sterile vessel;

enclosing the vessel such that the cell culture medium is not exposed to a surrounding environment;

adding nutrients to the contents of the vessel to support cell culture growth;

maintaining the contents of the vessel at a prescribed temperature to support cell culture growth;

introducing gas into the vessel to support cell culture growth;

mixing the contents of the container with a pneumatically-driven mixing element disposed within the vessel so as to be rotatable about a horizontal axis and being constructed and arranged to capture at least a portion of the gas introduced into the vessel and to be rotated by buoyant force of the captured gas to thereby effect mixing of the contents of the vessel, wherein the mixing element has at least one impeller blade located radially inward from an outer edge thereof configured to generate axial flow of at least a portion of the contents of the vessel upon rotation of the mixing element; and discarding the vessel and mixing element after a single cell culture growth process.

11. The method of claim 10, further comprising controlling the speed of rotation of the mixing element by controlling the rate of introduction of gas into the vessel.

12. The method of claim 10, wherein the gas is introduced at a location below the mixing element.

13. The method of claim 12, further comprising controlling the direction of rotation of the mixing element by introducing gas into the vessel below one side or the opposite side of the mixing element.

14. The method of claim 10, wherein the vessel is sterilized by exposing the vessel and the mixing element to gamma irradiation.

15. The method of claim 10, wherein the mixing element is configured to reduce force imposed on the mountings of the mixing element by generating toroidal flow of at least a portion of the contents of the vessel upon rotation of the mixing element.

16. The method of claim 10, wherein the vessel comprises a generally rectangular upper portion in horizontal section and a semi-cylindrical lower portion defining a semi-cylindrical concavity therewithin, and wherein the mixing element has a diameter such that when it rotates it substantially fills the semi-cylindrical concavity.

17. The method of claim 16, further including a rigid housing into which the vessel fits, the housing defining a semi-cylindrical lower section and the lower portion of the vessel being formed of a material that is non-structural such that the semi-cylindrical lower section of the housing structurally supports the vessel.

18. The method of claim 17, wherein a vessel top extends outwardly of vessel sides and rests on upper edges of the housing so as to suspend the vessel within the housing.

19. The method of claim 17, wherein the vessel is primarily formed of a thin wall film that is non-structural.

20. The method of claim 10, wherein the impeller is defined within an outer wheel on the mixing element.

* * * * *